United States Patent [19]

Wade et al.

[11] 4,104,387
[45] Aug. 1, 1978

[54] 3-(ARYLCYCLOIMINOALKYL)BENZISO-THIAZOLE 1,1-DIOXIDES

[75] Inventors: Peter C. Wade, Pennington; Thomas P. Kissick, Princeton, both of N.J.

[73] Assignee: E. R. Squibb & Sons, Inc., Princeton, N.J.

[21] Appl. No.: 799,865

[22] Filed: May 23, 1977

[51] Int. Cl.² .................. A61K 31/495; C07D 417/12
[52] U.S. Cl. ............................. 424/250; 260/293.57; 260/294.8 C; 260/301; 424/263; 424/267; 544/368
[58] Field of Search ............ 260/268 BC, 293.57, 260/301; 424/250, 263

[56] References Cited
U.S. PATENT DOCUMENTS

| 2,751,392 | 6/1956 | Grogan et al. | 260/301 |
| 3,787,411 | 1/1974 | Ruschig et al. | 260/268 PH |
| 4,000,274 | 12/1976 | Renth et al. | 424/250 |

Primary Examiner—Paul M. Coughlan, Jr.
Attorney, Agent, or Firm—Lawrence S. Levinson; Merle J. Smith; Burton Rodney

[57] ABSTRACT 3-(Arylcycloiminoalkyl)benzisothiazole 1,1-dioxides are provided having the structure

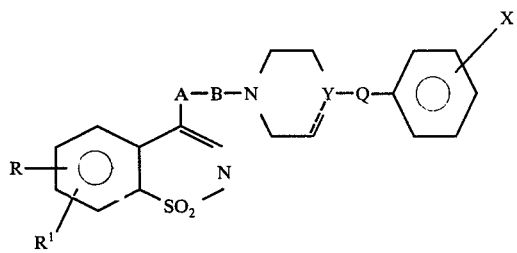

wherein R is hydrogen, halogen, lower alkyl, lower alkoxy or nitro; $R^1$ is hydrogen, lower alkoxy or halogen with the proviso that $R^1$ can be lower alkoxy or halogen only when R is lower alkoxy or halogen, respectively; A is O or NH; X is hydrogen, halogen lower alkyl, lower alkoxy, or trifluoromethyl; Y is C or N, where Y is C, is a double bond, and when Y is N, represents a single bond, B is an alkylene group containing 2 to 5 carbons in the normal chain; Q is a single bond or an alkylene group containing 1 to 3 carbons in the normal chain; and physiologically acceptable acid-addition salts thereof. These compounds are useful as antiinflammatory agents.

12 Claims, No Drawings

3-(ARYLCYCLOIMINOALKYL)BENZISO-THIAZOLE 1,1-DIOXIDES

FIELD OF THE INVENTION

The present invention relates to 3-(arylcycloiminoalkyl)-benzisothiazole, 1,1-dioxides which are useful as antiinflammatory agents.

DISCUSSION OF PRIOR ART

Pyrazolyl- and pyrazolinyl-1,2-benzisothiazole, 1,1-dioxides such as 3-(3-methylpyrazol-1-yl)-1,2-benzisothiazole, 1,1-dioxide and 3-(4-acetyl-3-methylpyrazol-1-yl)-1,2-benzisothiazole, 1,1-dioxide, are disclosed as hypotensive agents; see Traverso et al, "Hypotensive 1,2-benzisothiazole 1,1-dioxides, I. Pyrazole and Pyrazoline Derivatives," J. Med. Chem., Sept. 1967, Vol. 10, pp. 840–844.

U.S. Pat. No. 2,751,392 to Grogan et al discloses tertiary amine derivatives of N- and O-saccharin which are said to have been found suitable for the symptomatic relief of certain types of neuralgia, rheumatoid and arthritic disorders and to possess varying degrees of antihistaminic activity. The Grogan et al compounds are of the following three types:

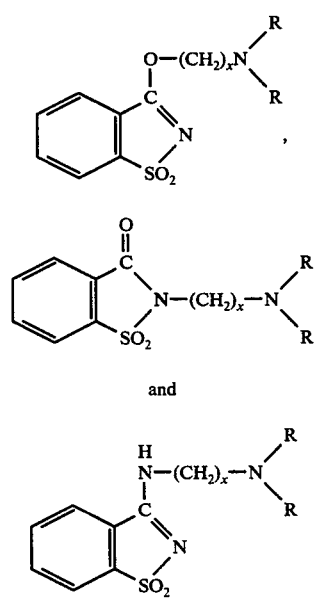

wherein x is 2 to 6, R is alkyl of 1 to 6 carbons or the grouping

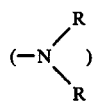

may represent pyrrolidine, morpholine and piperidine.

DESCRIPTION OF THE INVENTION

The 3-(arylcycloiminoalkyl)benzisothiazole, 1,1-dioxides of the invention have the structure

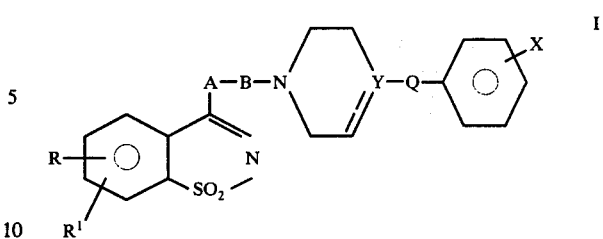

wherein R is hydrogen, lower alkyl, lower alkoxy, halogen or nitro; $R^1$ is hydrogen, lower alkoxy or halogen, $R^1$ can be lower alkoxy or halogen only when R is lower alkoxy or halogen, respectively, R and $R^1$ in such case preferably occupying the 5- or 6-positions, respectively; A is O or NH; B is an alkylene radical $(CH_2)_n$ containing 2 to 5 carbons in the normal chain, Q is a single bond or an alkylene radical $(CH_2)_m$ containing 1 to 3 carbons in the normal chain, Y is C or N;---represents the optional presence of a double bond which may be present when Y is C; and X is hydrogen, halogen, lower alkyl, lower alkoxy or trifluoromethyl.

Thus, the compounds of formula I of the invention may include compounds of the following structures:

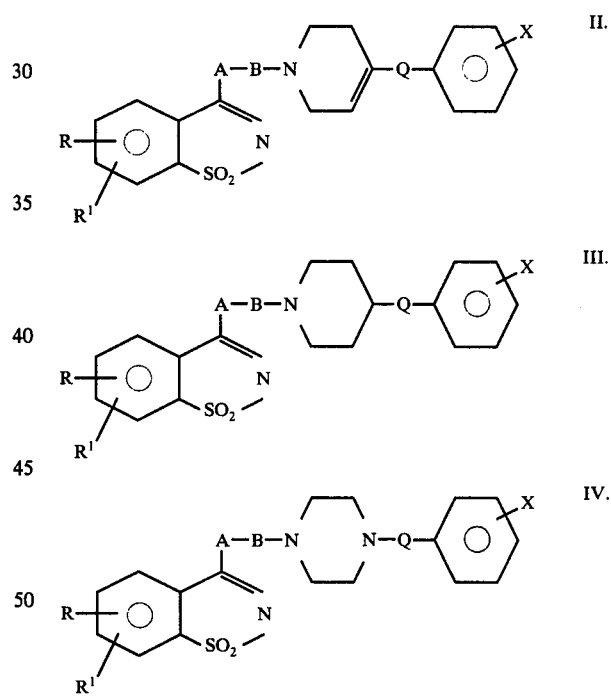

The preferred compounds of the invention are those of formula II wherein R is in the 5- or 6-position and $R^1$ is hydrogen or R and $R^1$ are hydrogen, A is NH, B is $(CH_2)_2$, Q is a single bond or $CH_2$, and those of formula IV wherein R is in the 5- or 6-position and $R^1$ is hydrogen or R and $R^1$ are hydrogen, A is O, B is $(CH_2)_2$, and Q is a single bond or $CH_2$.

The term "lower alkyl" as used herein refers to alkyl groups having 1 to 4 carbons, with methyl or ethyl being preferred.

The term "lower alkoxy" as used herein refers to lower alkyl groups as defined above attached to an oxygen atom, with methoxy being preferred.

The term "halogen" as employed herein refers to chlorine, bromine, iodine or fluorine with chlorine and bromine being preferred.

The compounds of Formulae I to IV of the invention may be prepared by heating a 3-substituted-1,2-benzisothiazole, 1,1-dioxide of the structure

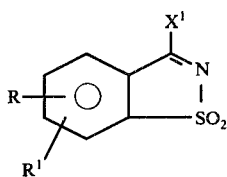

V.

wherein $X^1$ is Cl, Br, lower alkoxy, lower alkylthio or mercapto (SH), with an amine of the structure

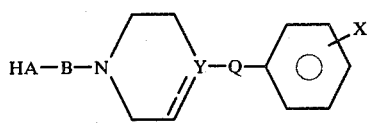

VI.

in the presence of an aprotic solvent, such as acetone methyl ethyl ketone, dioxane, dimethylformamide, and the like.

The starting material V in the above reaction may be prepared by reaction of a saccharin compound of the structure

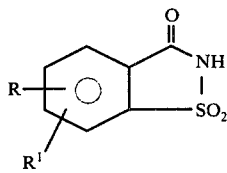

VII with a dehydrating agent, such as thionyl chloride in the presence of a non-reacting solvent, such as dioxane, benzene or THF in the optional presence of a catalyst, such as dimethylformamide.

The starting materials of Formula VI are known in the art or may be prepared by a variety of conventional techniques.

Depending on the reaction conditions and the starting materials used, the new compounds are obtained in the free form or in the form of their acid-addition salts. The salts thereof can be converted into the free compounds in a known manner such as by reaction with a basic agent. Free bases which may be obtained can be converted into pharmaceutically acceptable acid-addition salts by reaction with a variety of acids. Acids useful for preparing these acid-addition salts include, inter alia, inorganic acids, such as the hydrohalic acids (e.g., hydrochloric and hydrobromic acids), sulfuric acid, nitric acid, and phosphoric acid, and organic acids, such as maleic, fumaric, tartaric, citric, acetic, benzoic, 2-acetoxybenzoic, salicyclic, succinic, nicotinic, methanesulfonic or cyclohexanesulfamic.

The compounds of formula I have antiinflammatory activity as measured by the reverse passive arthus (RPA) or other related tests (M. B. Goldlust and W. F. Schreiber, Agents and Action, 5, 39 (1975) and/or other related tests and are useful as antiinflammatory agents and may be used, for example, in a manner similar to phenylbutazone or indomethacin. They may be used to decrease joint swelling, tenderness, pain and stiffness in mammalian species, e.g., in conditions such as rheumatoid arthritis. The quantity administered ranges from about 1 mg to about 150 mg per kg of body weight per day.

For the above pharmaceutical purposes a compound or mixture of compounds of formula I or their pharmaceutically acceptable acid-addition salts may be administered orally or parenterally in a conventional dosage form, such as tablet, capsule, injectable or the like. These may be conventionally formulated in an oral or parenteral dosage form by compounding with a conventional vehicle, excipient, binder, preservative, stabilizer, flavor or the like as called for by accepted pharmaceutical practice.

The following examples are illustrative of the invention and represent preferred embodiments. Other modifications may be readily produced by suitable variations of the reactions. All temperatures are on the Centigrade scale.

EXAMPLE 1

3-[2-(4-Phenyl-1-piperazinyl)ethoxy]-1,2-benzisothiazole, 1,1-dioxide, hydrochloride (1:1)

A. 3-Chloro-1,2-benzisothiazole-1,1-dioxide (Pseudo saccharin chloride)

Reference: Japanese Pat. No. 048934

100 g (545 mM) Saccharin, 100 ml thionyl chloride, 4 ml dimethylformamide (DMF) (catalyst), and 400 ml dioxane are refluxed overnight. Thionyl chloride (50 ml) and DMF (1 ml) are added to the reaction mixture which is refluxed overnight again. The reaction mixture is evaporated and the residue recrystallized from toluene to yield 73.4 g, m.p. 140°–145° [lit. m.p. 148°–149°].

B.

3-[2-(4-Phenyl-1-piperazinyl)ethoxy]-1,2-benzisothiazole, 1,1-dioxide, hydrochloride (1:1)

13.2 g (65.5 mM) 3-Chloro-1,2-benzisothiazole, 1,1-dioxide (prepared as described in part A) dissolved in 150 ml acetone, is added to 13.5 g (65.5 mM) 4-phenyl-1-piperazineethanol, dissolved in 150 ml acetone, dropwise over 15 minutes. The mixture is refluxed for 30 minutes. After stirring for 1 hour at room temperature, a precipitate forms which is filtered out and washed with acetone, and dried at 80°/vacuum to give 23.4 g of the above titled compound. The compound softens at about 190° and melts at approximately 270° with decomposition.

EXAMPLE 2

N-[2-(3,6-Dihydro-4-phenyl-1(2H)-pyridinyl)ethyl]-1,2-benzisothiazol-3-amine, 1,1-dioxide 5.51 g (27.3 mM) 3,6-Dihydro-4-phenyl-1(2H)-pyridineethanamine, dissolved in 30 ml dioxane is added to 5.0 g (24.8 mM) 3-chloro-1,2-benzisothiazole, 1,1-dioxide prepared as described in Example 1A dissolved in 50 ml acetone. This mixture is refluxed for 30 minutes. A precipitate forms which is filtered out after standing for 2 hours at room temperature, and taken up in a mixture of 10% NaOH and chloroform. The chloroform layer is washed with water and evaporated. The residue is recrystallized from ethanol to give 5.73 g of the title compound, m.p. 231°–232°.

EXAMPLES 3 TO 17

Following the procedure of Example 2, but substituting for the 3-chloro-1,2-benzisothiazole, 1,1-dioxide, the compound shown in column II of Table A below, and substituting for the 3,6-dihydro-4-phenyl-1(2H)-pyridineethanamine, the compound shown in Column I, the compound of the invention shown in Column III is obtained.

TABLE A

| Ex. No. | Column I | Column II R (position) | Column II R¹ (position) | Column II X¹ | Column III |
|---|---|---|---|---|---|
| | HA—B—N⟨ ⟩Y—O—⟨phenyl-X⟩ | (structure with A—B—N, ring with R, R¹, and C=CH₂/SO₂ group, X¹) | | | As in Column I / As in Column II |
| 3. | HO—(CH₂)₂—N⟨ ⟩=⟨phenyl-OCH₃, X⟩ | NO₂(5) | H | Cl | |
| 4. | HO—(CH₂)₅—N⟨ ⟩—CH₂—⟨phenyl-CH₃⟩ | NO₂(4) | H | Br | |
| 5. | H₂N—(CH₂)₅—N⟨ ⟩=⟨phenyl-Cl⟩ | Cl(5) | H | Cl | |
| 6. | H₂N—(CH₂)₂—N⟨ ⟩—CH₂—⟨phenyl-CF₃⟩ | Cl(7) | H | Cl | |
| 7. | HO—(CH₂)₃—N⟨ ⟩N—(CH₂)₂—⟨phenyl⟩ | Cl(5) | Cl(6) | Cl | |

TABLE A-continued

| Ex. No. | Column I | Column II R (position) | R¹ (position) | X¹ | Column III |
|---|---|---|---|---|---|
| 8. | H₂N—(CH₂)₂—N(piperazine)-phenyl | Br(6) | H | CH₃O | |
| 9. | HO—(CH₂)₂—N(piperazine)-CH₂-(3-CF₃-phenyl) | F(5) | H | SH | |
| 10. | HO—(CH₂)₃—N(piperazine)-(CH₂)₃-phenyl | CH₃(6) | H | CH₃O | |
| 11. | H₂N—(CH₂)₅—N(piperidine)-(CH₂)₂-phenyl | i-propyl(6) | H | CH₃O | |
| 12. | H₂N—(CH₂)₄—N(piperidine)-(4-CH₃-phenyl) | CH₃O(5) | H | Cl | |
| 13. | HO—(CH₂)₄—N(piperidine)-CH₂-(4-Cl-phenyl) | Cl(5) | Cl(6) | Cl | |

TABLE A-continued

| | Column I | Column II | | | Column III | | |
|---|---|---|---|---|---|---|---|
| Ex. No. | HA—B—N⟨ring⟩Y—O—⟨ring-X⟩ | R (position) | $R^1$ (position) | $X^1$ | A—B—N⟨ring⟩Y—O—⟨ring-X⟩ | R (position) | $R^1$ (position) |
| 14. | HO—(CH$_2$)$_3$—N⟨piperidine⟩—⟨C$_6$H$_4$-Br⟩ | CH$_3$O(5) | CH$_3$O(6) | Cl | | | |
| 15. | HO—(CH$_2$)$_2$—N⟨piperazine⟩—⟨C$_6$H$_4$-C$_2$H$_5$⟩ | NO$_2$(7) | H | Br | | | |
| 16. | H$_2$N—(CH$_2$)$_3$—N⟨piperazine⟩—CH$_2$—⟨C$_6$H$_5$⟩ | CH$_3$(6) | H | Cl | | | |
| 17. | H$_2$N—(CH$_2$)$_5$—N⟨piperidine⟩—⟨C$_6$H$_5$⟩ | CH$_3$(7) | H | Cl | | | |

What is claimed is:

1. A compound of the structure

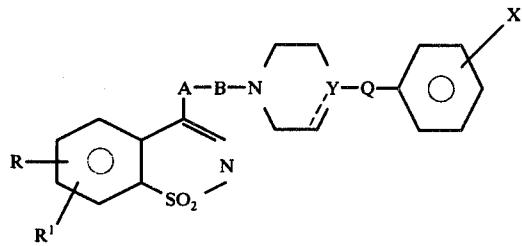

wherein R is hydrogen, halogen, lower alkyl, lower alkoxy or nitro; $R^1$ is hydrogen, lower alkoxy or halogen with the proviso that $R^1$ can be lower alkoxy or halogen only when R is lower alkoxy or halogen, respectively; A is O or NH; X is hydrogen, halogen, lower alkyl, lower alkoxy, or trifluoromethyl; Y is C or N, where Y is C, --- represents a double bond, and when Y is N, --- represents a single bond, B is an alkylene group containing 2 to 5 carbons in the normal chain; Q is a single bond or an alkylene group containing 1 to 3 carbons in the normal chain; and physiologically acceptable acid-addition salts thereof.

2. The compound of claim 1 having the structure

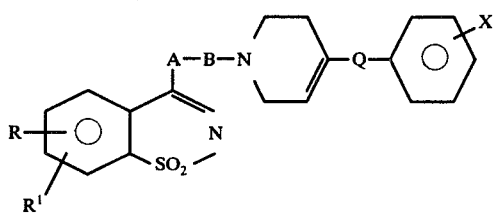

3. The compound of claim 1 having the structure

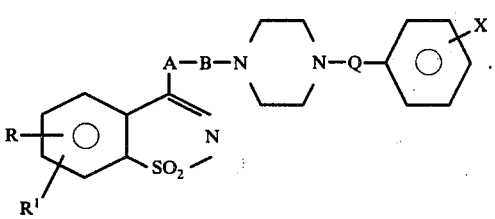

4. The compound of claim 2 wherein R is hydrogen, A is NH, B is $(CH_2)_2$, Q is a single bond or $CH_2$, and X is hydrogen.

5. The compound of claim 3 wherein R is hydrogen, A is O, B is $(CH_2)_2$, Q is a single bond or $CH_2$, and X is hydrogen.

6. The compound of claim 1 wherein A is —$(CH_2)_2$— or —$(CH_2)_3$— and Q is a single bond or $CH_2$.

7. The compound of claim 1 wherein $R^1$ is hydrogen.

8. The compound of claim 7 wherein R is in the 5- or 6-position.

9. The compound of claim 1 having the name 3-[2-(4-phenyl-1-piperazinyl)ethoxy]-1,2-benzisothiazole, 1,1-dioxide or its hydrochloride salt.

10. The compound of claim 1 having the name N-[2-(3,6-dihydro-4-phenyl-1(2H)-pyridinyl)ethyl]-1,2-benzisothiazol-3-amine, 1,1-dioxide.

11. A composition which comprises a compound of claim 1 in a physiologically acceptable vehicle, said compound being present in an effective amount for treating an inflammatory condition.

12. A method for treating an inflammatory condition in a mammalian host, comprises administering an effective amount of the composition of claim 11.

* * * * *

UNITED STATES PATENT AND TRADEMARK OFFICE
CERTIFICATE OF CORRECTION

PATENT NO. : 4,104,387
DATED : August 1, 1978
INVENTOR(S) : Peter C. Wade et al

It is certified that error appears in the above-identified patent and that said Letters Patent are hereby corrected as shown below:

In the Abstract, "where Y is C, is a double bond, and when Y is N," should read --where Y is C, ==== is a double bond, and when Y is N, ==== --.

Column 1, line 7, delete the hyphen before "benzisothiazole".

Signed and Sealed this

Sixteenth Day of January 1979

[SEAL]

Attest:

RUTH C. MASON
*Attesting Officer*

DONALD W. BANNER
*Commissioner of Patents and Trademarks*